United States Patent
Schöndube et al.

(10) Patent No.: US 8,606,038 B2
(45) Date of Patent: Dec. 10, 2013

(54) METHOD AND COMPUTER SYSTEM FOR THE REDUCTION OF ARTIFACTS IN RECONSTRUCTED CT IMAGE DATASETS

(75) Inventors: Harald Schöndube, Erlangen (DE); Karl Stierstorfer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 129 days.

(21) Appl. No.: 13/358,624

(22) Filed: Jan. 26, 2012

(65) Prior Publication Data

US 2012/0195483 A1    Aug. 2, 2012

(30) Foreign Application Priority Data

Jan. 27, 2011    (DE) .......................... 10 2011 003 240

(51) Int. Cl.
| | |
|---|---|
| G06K 9/40 | (2006.01) |
| G06K 9/00 | (2006.01) |
| A61B 6/00 | (2006.01) |
| G01N 23/00 | (2006.01) |
| G21K 1/12 | (2006.01) |
| H05G 1/60 | (2006.01) |

(52) U.S. Cl.
USPC ............... 382/275; 382/131; 382/132; 378/4; 378/15; 378/21

(58) Field of Classification Search
USPC .................. 382/131, 132, 275; 378/4, 15, 21
See application file for complete search history.

(56) References Cited

U.S. PATENT DOCUMENTS

| | | | | |
|---|---|---|---|---|
| 6,047,039 | A * | 4/2000 | Flohr ............................... | 378/4 |
| 7,391,927 | B2 * | 6/2008 | Stierstorfer ................... | 382/275 |
| 7,866,884 | B2 * | 1/2011 | Seto ............................... | 378/207 |
| 8,260,017 | B2 * | 9/2012 | Ohishi et al. ................... | 382/128 |
| 2004/0028173 | A1 * | 2/2004 | van de Haar ...................... | 378/4 |
| 2005/0111611 | A1 | 5/2005 | Hein et al. | |

FOREIGN PATENT DOCUMENTS

| | | |
|---|---|---|
| DE | 19835451 A1 | 3/1999 |
| DE | 19835451 B4 | 3/2005 |

OTHER PUBLICATIONS

Kumar et al., "A mixed approach to artifacts minimization in a continuous-rotate X-ray based tomographic imaging system using linear detector array", Applied Radiation and Isotopes 57 (2002) 543-555, 2002.*
Hein et al., "Feldkamp-based cone-beam reconstruction for gantry-tilted helical multislice CT", Med. Phys. 30 (12), Dec. 2003.*
German Office Action for German Application No. DE 10 2011 003 240.1 (Not Yet Published).
Certified German Priority document for German Application No. DE 10 2011 003 240.1 (Not Yet Published).

* cited by examiner

*Primary Examiner* — Anand Bhatnagar
*Assistant Examiner* — Soo Park
(74) *Attorney, Agent, or Firm* — Harness, Dickey & Pierce, P.L.C.

(57) ABSTRACT

A method and computer system are disclosed with software for artifact reduction in CT image datasets for spiral scans from a CT system with an inclined gantry. In at least one embodiment, for each of at least two positions of the center of rotation, which is moved during the spiral scan, the removal of annular artifacts is carried out around these positions, during which the position concerned is used as the center point of the annular artifacts to be removed.

14 Claims, 3 Drawing Sheets

METHOD AND COMPUTER SYSTEM FOR THE REDUCTION OF ARTIFACTS IN RECONSTRUCTED CT IMAGE DATASETS

PRIORITY STATEMENT

The present application hereby claims priority under 35 U.S.C. §119 to German patent application number DE 10 2011 003 240.1 filed Jan. 27, 2011, the entire contents of which are hereby incorporated herein by reference.

FIELD

At least one embodiment of the invention generally relates to a method and/or a computer system for the reduction of artifacts in reconstructed CT image datasets which arise in a typical embodiment as a result of defective detector pixels.

BACKGROUND

A method for the reduction of artifacts in reconstructed CT image datasets which arise as a result of defective detector pixels in the case of simple circular scans, is known from the publication DE 198 35 451 B4 (=U.S. Pat. No. 6,047,039), for example. However, in the case of the method presented there, only artifacts which are exactly circular in shape, such as arise with defective detector pixels in conjunction with circular scans, are removed.

In the case of an image reconstruction from detector data which has been obtained in the context of a spiral scan with the gantry being at the same time inclined, any artifacts produced are not exactly circular in shape, so that the application of the method for artifact reduction known from the publication DE 198 35 451 B4 is not enough to remove such artifacts.

SUMMARY

In at least one embodiment of the invention, a method is disclosed for the reduction of artifacts in reconstructed CT image datasets, which arise in a typical embodiment as a result of defective detector pixels, which can be successfully applied to CT image datasets from spiral scans with the gantry being at the same time inclined or with an axis of rotation which is inclined relative to the system axis, as applicable.

Advantageous developments of the invention are the subject of the claims.

The inventors have recognized the following:

In the course of CT image reconstruction, defective detector channels usually result in annular artifacts in the image. These artifacts are arranged around a common center point which is identical in the image with the position of the isocenter, that is the center of rotation of the gantry. Because it is impossible, for technical reasons, to completely exclude minor defects in the detector, under the prior art there is typically, as part of the image reconstruction 'pipeline' for medical CT devices, a correction step which is also referred to as "balancing", which is intended to remove these artifacts.

In the case of a spiral trajectory (spiral CT), complete rings will typically not appear, but only partial rings. Common to all situations, however, is the same center point at the isocenter, so that the balancing algorithms can be applied in both cases.

However if, during the recording of the CT data, the gantry is inclined relative to the system axis or to the table advance axis, as applicable, this feature, the shared center point for the annular artifacts, no longer applies. An artifact arising during this type of scan corresponds in the image to a spiral with a center point which moves during the scan, so that the known methods for artifact reduction become ineffective.

However, as the inventors have recognized, it is possible to modify the essential features of the known method to the effect that annular artifacts can continue to be sought and removed, but with the selection for these annular artifacts of several reference points, that is their center points, on a line which is defined in the CT image dataset by the point of intersection between the system axis and the axis of rotation, which moves during the scan. This multiple elimination of circular structures about several center points also effects a step by step removal of the spiral-shaped artifacts.

Accordingly, in at least one embodiment, the inventors propose a method for artifact reduction in CT image datasets from inclined spiral scans by a CT system with a gantry which can be moved along a system axis which has an axis of rotation, wherein the axis of rotation forms an acute angle with the system axis, wherein the following method steps are executed:

performance of a spiral scan of an object with the axis of rotation of gantry being at the same time inclined relative to the system axis, reconstruction of at least one CT image dataset from detector data which has been collected during a finite advance along the system axis, wherein image artifacts arising from defective detector pixels can be present in this at least one CT image dataset, determination of the geometric position of the line in the reconstructed image dataset which connects all the points of intersection between the system axis and the axis of rotation during the scan, selection of at least two points in the CT image dataset which are on the connecting line, and performance in each case of a removal of annular artifacts about each of the selected points, wherein the point concerned is used as the center point of the annular artifacts which are to be removed.

It is advantageous with this method if, from the CT image dataset, at least one artifact image dataset is calculated by multiple filtering, this containing only the image artifacts which arise from defective detector pixels, the at least one artifact image dataset is subtracted pixel-by-pixel from the CT image dataset, and the result is displayed and/or stored and/or is further processed.

In doing this, it is expedient to calculate the artifact image dataset for each selected center point by the execution of the following method steps:

performance of median-high-pass filtering in the radial direction relative to the particular center point under consideration, followed by a plurality of low pass filtering operations in the angular direction along arcs of various radii about the center point concerned.

It is also particularly expedient to include a threshold filtering operation and to calculate the artifact image dataset for each selected center point by the execution of the following method steps:

performance of a threshold filtering operation on the CT image dataset, followed by a median-high-pass filtering operation in the radial direction relative to the particular center point under consideration, followed by another threshold filtering operation, followed by a plurality of low pass filtering operations in the angular direction along arcs of various radii about the center point concerned.

By this, a median filtering operation is performed on the original image in the radial direction, this representing a type of low pass filtering. If one then deducts the median filtered image from the original image, one obtains a median-high-pass filtered image in which only edges which are perpendicular to the radial direction of filtering are now still contained. In order now to distinguish bone edges, for example, from annular artifacts, there follow the formation of thresholds, wherein it is assumed that an artifact does not exceed a certain threshold, and low-pass filtering in the angular direction, that is, along the presumed annular artifacts.

Furthermore, a separate artifact image dataset can be generated for each selected center point in each CT image dataset, and the artifact image datasets can be subtracted individually from the CT image dataset.

Alternatively, an artifact image dataset can also be generated for each selected center point in each CT image dataset, these can be added together and the resulting overall artifact image dataset for all the selected center points can be subtracted from the CT image dataset.

In most practical cases of an embodiment of the method presented above, it is sufficient if two or three center points are selected for each CT image dataset.

In addition to embodiments of the inventive method, the ambit of at least one embodiment of the invention also covers a computer system, in a CT system with an axis of rotation for a gantry which can be inclined relative to a system axis, having a memory for computer programs which also contains a computer program which, in operation, performs at least the following:

receipt of detector data from a spiral scan of an object with the axis of rotation of the gantry being at the same time inclined relative to the system axis, reconstruction of at least one CT image dataset from detector data which has been collected during a finite advance along the system axis, wherein image artifacts arising from defective detector pixels can be present in this at least one CT image dataset, determination of the geometric position of the line in the reconstructed image dataset which connects all the points of intersection between the system axis and the axis of rotation during the scan, selection of at least two points in the CT image dataset which are on the connecting line, and performance in each case of a removal of annular artifacts about each of the selected points, wherein the point concerned is used as the center point of the annular artifacts which are to be removed.

Finally, the ambit of at least one embodiment of the invention also covers a computer system, which may be freestanding or may be linked to a CT system via a network line, which is designed for image processing and is provided with a memory for computer programs, wherein the memory also contains a computer program which, in operation, performs at least the following:

receipt of at least one CT image dataset from detector data from spiral sampling with an inclined gantry, wherein image artifacts arising from defective detector pixels can be present in this at least one CT image dataset, determination of the geometric position of the line in the reconstructed image dataset which connects all the points of intersection between the system axis and the axis of rotation during the scan, selection of at least two points in the CT image dataset which are on the connecting line, and performance in each case of a removal of annular artifacts about each of the selected points, wherein the point concerned is used as the center point of the annular artifacts which are to be removed.

In both of the computer systems described above, computer programs can then also be stored which, in operation, can execute the steps described above.

BRIEF DESCRIPTION OF THE DRAWINGS

Embodiments of the invention are described in more detail below with the aid of figures, in which are shown only the features necessary for an understanding of the invention. The following reference marks are used: 1: CT system; 2: first X-ray tube; 3: first detector; 4: second X-ray tube; 5: second detector; 6: gantry housing; 7: patient; 8: patient table; 10: computer system; 11: contrast agent applicator; 12: ECG line; $A_1, A_2, A_3$: artifact lines; B: CT image; BE: image plane; D: detector; F: focus; L: connecting line; M: measurement field; $M_1, N_2, M_3$: center points; O: object; $Prg_1$ to $Prg_n$: computer programs; $S_1$; $S_n$: peripheral rays; x: horizontal transverse axis; y: vertical perpendicular axis; y': perpendicular to the axis of rotation; z: system axis; z': inclined axis of rotation; δ: angle.

Shown in detail are.

DETAILED DESCRIPTION OF THE EXAMPLE EMBODIMENTS

Figure 1:
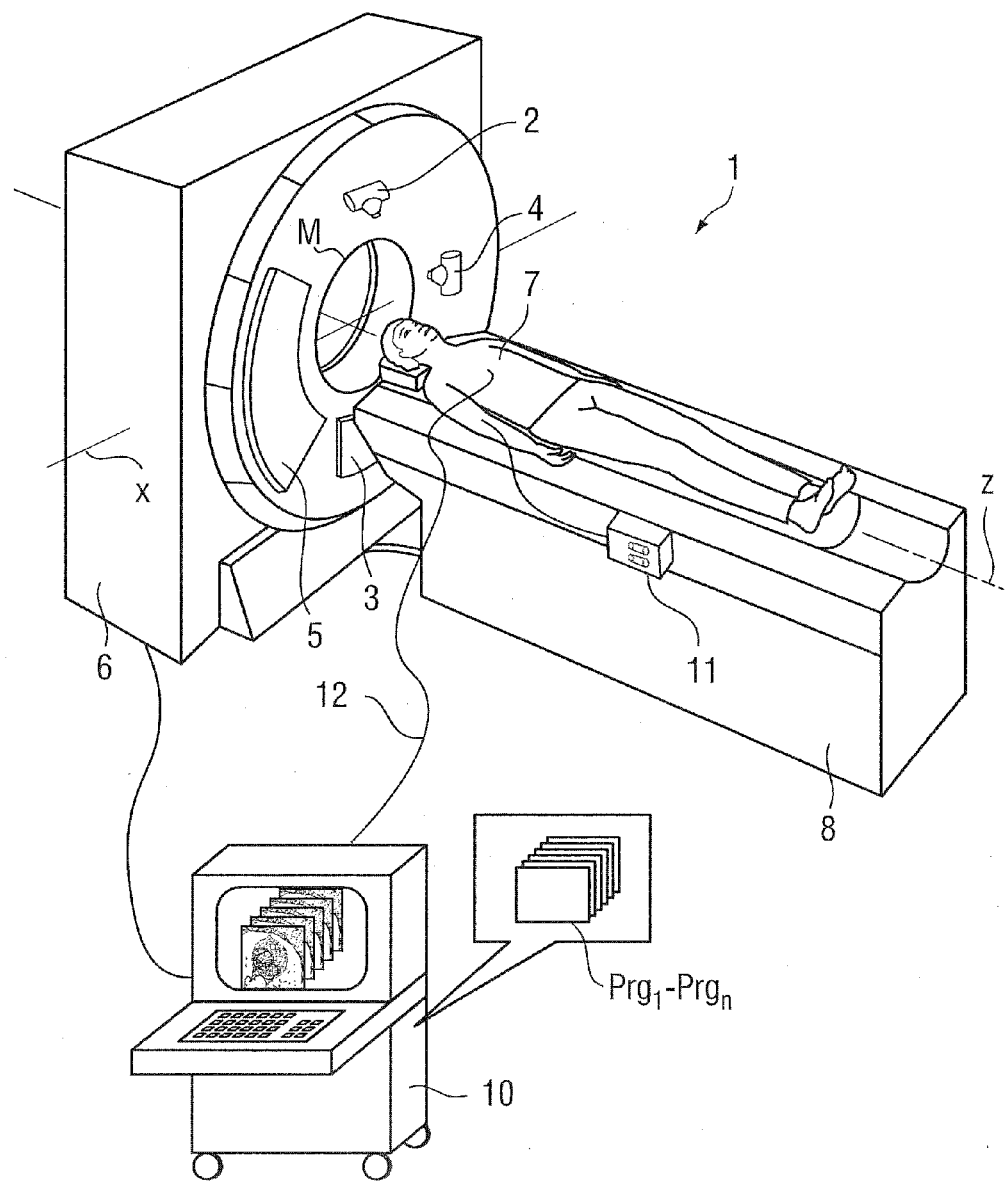
FIG. 1 is an example of a CT system for performing an embodiment of the inventive method.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 shows a CT system 1 in accordance with an embodiment of the invention, with a gantry housing 6 in which are located, on a gantry which is not shown in more detail here, an X-ray tube 2 with a detector 3 on the opposite side, which when in operation rotates about an axis of rotation for the gantry. The gantry itself is constructed so that it can be inclined about a horizontal transverse axis x, so that a patient 7, who is located on a patient table 8, can be scanned in an appropriately oblique plane. For this scan, the patient table 8 is used to move the patient 7 steadily along a system axis z through the measurement field M of the gantry, while at the same time a scan of body of the patient 7 is made using the radiator/detector system, consisting of the X-ray tube 2 and detector 3. As an option, there is a possibility of mounting in addition a second radiator/detector system on the gantry. This is represented here by the second X-ray tube 4 and the second detector 5 which is on the opposite side from this X-ray tube.

The CT system 1 has in addition a computer system 10, which is used on the one hand to control the CT system 1, and for this purpose has computer programs $Prg_1$ to $Prg_n$ stored in its memory. This computer system 10 can in addition be used as an ECG system, which with the aid of an ECG line 12 can record the heart rhythm of the patient 7 and can thereby influence the control of the sampling of the patient 7. In addition, the illustration of the CT system 1 shown here also shows a contrast agent applicator 11, with which contrast agents can be injected into the patient for better contrast between organic structures.

In accordance with an embodiment of the invention there is also, among the programs $Prg_1$ to $Prg_n$, at least one program which can perform an embodiment of the inventive method for the reduction of annular artifacts when it is applied to reconstructed image data which can also be calculated by the computer system 10.

Figure 2:
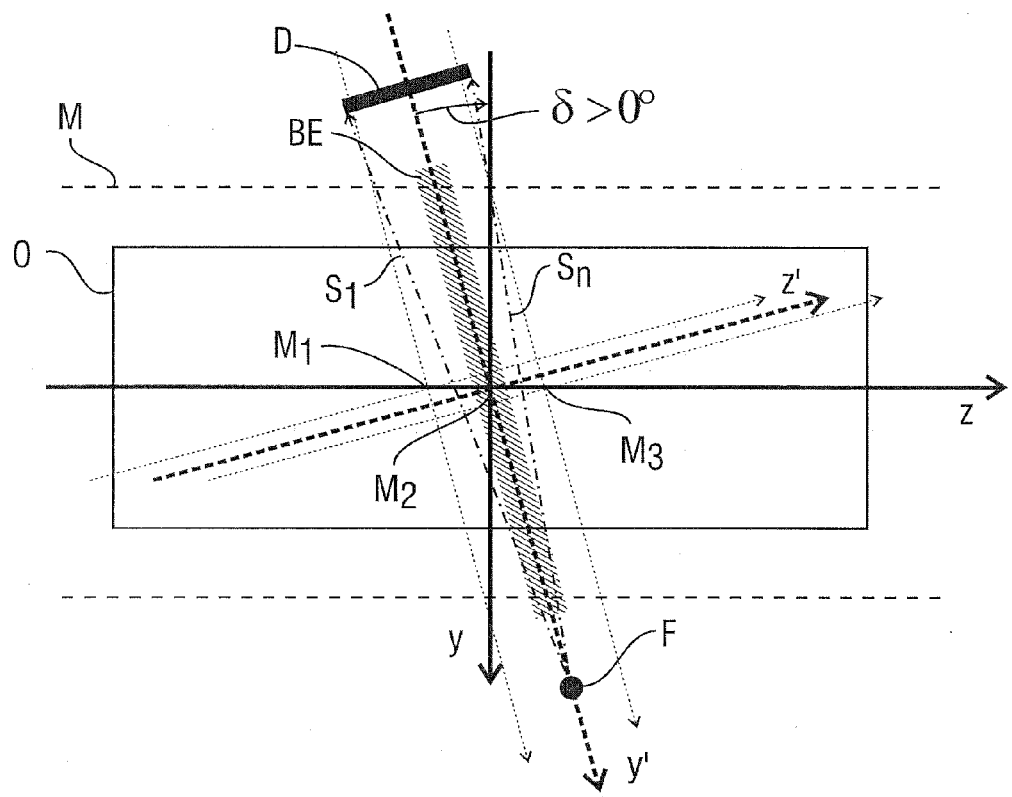
FIG. 2 is a schematic representation of the reference system in a section through a CT system.

For the purpose of clarifying an embodiment of the inventive method, FIG. 2 is a schematic section through a cylindrical-shaped object O under investigation, which is aligned with its longitudinal axis parallel to the z-axis of the CT system's coordinate system. In addition, the y-axis of this coordinate system is also shown. Perpendicular to the section through the z-axis and the y-axis is the x-axis of this coordinate system, which is identical with the transverse axis x in FIG. 1. Also shown is the z-axis, identical with the system axis z in FIG. 1, and the usable measurement field M bounded by two dashed lines.

Further, FIG. 2 shows schematically a radiator/detector system consisting of a focus F, from which a beam of rays—indicated by the edge rays $S_1$ and $S_n$—is aligned towards the detector D on the opposite side. The gantry, on which are arranged the focus F and the detector D, is in the present case inclined at an angle δ, which is greater than zero, about the x-axis, not shown, so that the plane of rotation of the gantry, which is represented by the inclined y'-axis, adopts this angle 5 to the y-axis during the scan. The new axis of rotation of the gantry is identified in the present diagram by z'. The y'-axis and the z'-axis are each shown dashed. For the purpose of clarifying the execution of a spiral scan in accordance with an embodiment of the invention, which is carried out over a certain period of time during which the gantry is here moved relative to the object O which is to be scanned, the diagram includes to the left and the right of the actual inclined coordinate system the corresponding coordinate systems at the start and at the end of the scan—shown as thin dotted lines. Here, the origins of the coordinates all lie on the z-axis (system axis) and at the same time determine examples of selected center points $M_1$ to $M_3$. Also shown along the y'-axis is a hatched area BE, which shows the image plane which will later be shown in a reconstructed cross-sectional image.

Figure 3:
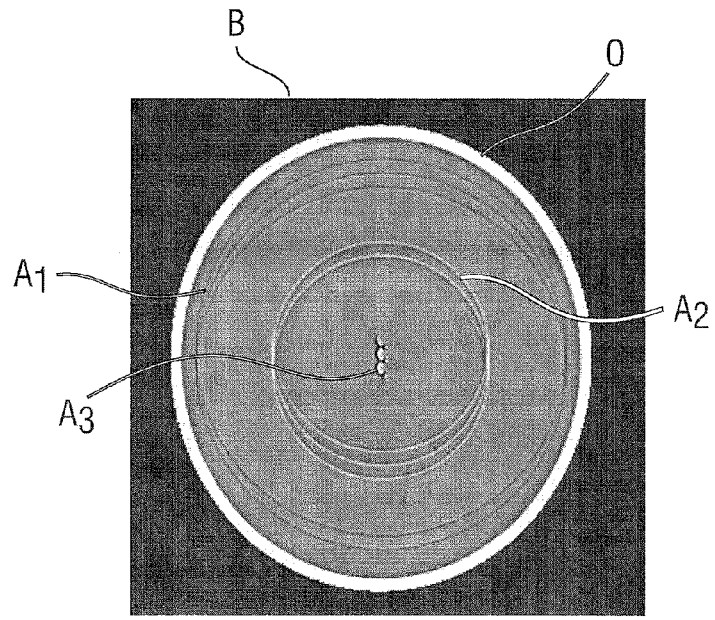
FIG. 3 is an illustration of a CT image dataset for a recording from a cylindrical object, with a simulation of three defective detector pixels.

If such a scan is carried out with an inclined gantry and with three defective detector pixels, the result will be a recording of this object O as shown in FIG. 3 beneath. FIG. 3 shows a CT image B in which the object O—in this case a water-filled plexi-glass cylinder (white border=plexi-glass, grey interior=water)—which is per se cylindrical in shape has an oval contour, because of the oblique section, wherein three artifact traces $A_1$, $A_2$ and $A_3$ are shown in the illustration of the cylindrical-shaped object.

Figure 4:
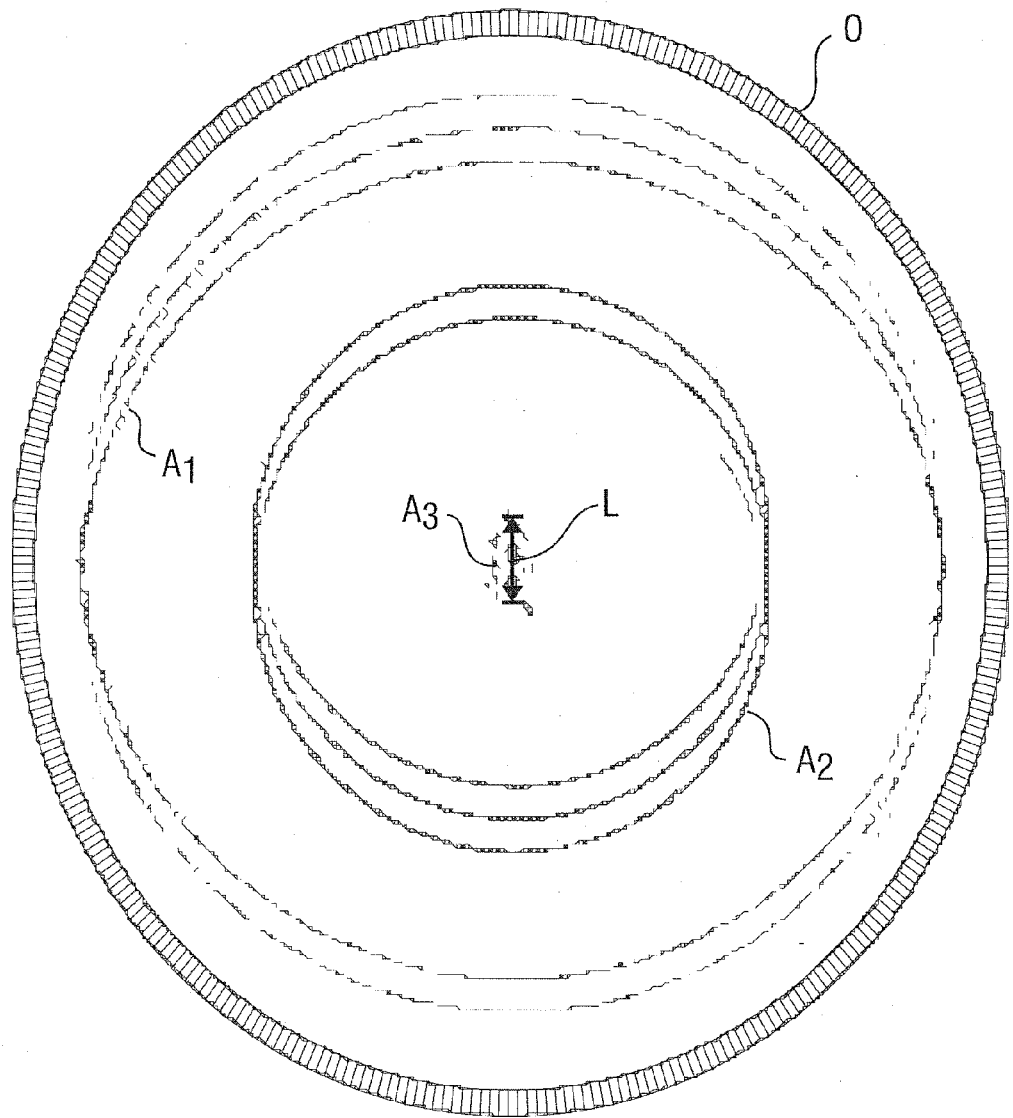
FIG. 4 is a vectorized representation of the image in FIG. 3.

To give a clearer presentation, this representation in image form of the object O is redrawn in FIG. 4 in vectorized form, wherein a gray-scale representation has here been forgone and a purely black-and-white representation enables the artifact traces $A_1$ to $A_3$ to be recognized again particularly well.

In accordance with an embodiment of the invention a line L is now sought, in an image of this type, on which are located the rays which pass through the center points $M_1$ to $M_3$—not drawn in here. An artifact reduction method for the removal of annular artifacts, which is known per se, is then performed around several selected center points lying on this line L. In practice it has been found that the application of two or three known artifact removal methods about two or three center points on the line L are adequate to produce good elimination of the artifacts.

Overall, an embodiment of the invention thus proposes a method and a computer system with software for the reduction of artifacts in CT image datasets for spiral scans from a CT system with an inclined gantry, wherein for each of at least two positions of the center of rotation, which is moved during the spiral scan, the removal of annular artifacts is carried out around these positions, in doing which the position concerned is used as the center point of the annular artifacts to be removed.

It goes without saying that the features of embodiments of the invention cited above can not only be used in the particular combination stated, but also in other combinations or in isolation, without going outside the ambit of the invention.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method, comprising:

performing a spiral scan of an object, using a CT system with a gantry which is movable along a system axis, an axis of rotation of the gantry being inclined relative to the system axis during the spiral scan and the axis of rotation forming an acute angle to the system axis;

reconstructing at least one CT image dataset from detector data collected during a finite advance along the system axis, wherein image artifacts arising from defective detector pixels may be present in the at least one CT image dataset;

determining a geometric position of a line, in the reconstructed at least one CT image dataset, which connects points of intersection between the system axis and the axis of rotation during the performed scan;

selecting at least two points in the at least one CT image dataset which are on the connecting line; and performing a removal of annular artifacts about each of the selected at least two points, wherein each of the at least two points are used as a center point of the annular artifacts to be removed.

2. The method as claimed in claim 1, wherein
from the at least one CT image dataset, at least one artifact image dataset is calculated by multiple filtering, containing only the image artifacts which arise from defective detector pixels;
the at least one artifact image dataset is subtracted pixel-by-pixel from the at least one CT image dataset; and
a result of the subtraction is at least one of displayed, stored and further processed.

3. The method as claimed in claim 2, wherein the at least one artifact image dataset is calculated for each selected center point by execution of one or more of the following:
performing a median-high-pass filtering operation in the radial direction relative to the center point;
performing a plurality of low pass filtering operations in the angular direction along arcs of various radii about the center point.

4. The method as claimed in claim 2, wherein the at least one artifact image dataset is calculated for each selected center point by execution of one or more of the following:
performing a threshold filtering operation on the at least one CT image dataset;
performing a median-high-pass filtering operation in the radial direction relative to the selected center point;
performing another threshold filtering operation;
performing a plurality of low pass filtering operations in the angular direction along arcs of various radii about the center point concerned.

5. The method as claimed in claim 2, wherein an artifact image dataset is generated for each selected center point in each at least one CT image dataset, wherein the generated artifacts are added together to form a resulting overall artifact image dataset and wherein the resulting overall artifact image dataset for all the selected center points is subtracted from the CT image dataset.

6. The method as claimed in claim 2, wherein two or three center points are selected for each at least one CT image dataset.

7. The method as claimed in claim 1, wherein an artifact image dataset is generated for each selected center point in each at least one CT image dataset and wherein the artifact image datasets are subtracted individually from the CT image dataset.

8. The method as claimed in claim 1, wherein an artifact image dataset is generated for each selected center point in each at least one CT image dataset, wherein the generated artifacts are added together to form a resulting overall artifact image dataset and wherein the resulting overall artifact image dataset for all the selected center points is subtracted from the CT image dataset.

9. The method as claimed in claim 1, wherein two or three center points are selected for each at least one CT image dataset.

10. A non-transitory computer readable medium including program segments for, when executed on a computer device, causing the computer device to implement the method of claim 1.

11. A computer system in a CT system including an axis of rotation for a gantry which is inclinable relative to a system axis, comprising:
a memory to store a computer program which, in operation, is adapted to perform at least the following
receipt of detector data from a spiral scan of an object, the axis of rotation of the gantry being at inclined relative to the system axis during the spiral scan,
reconstruction of at least one CT image dataset from the detector data collected during a finite advance along the system axis, wherein image artifacts arising from defective detector pixels may be present in the at least one CT image dataset,
determination of a geometric position of a line, in the reconstructed at least one CT image dataset, which connects all points of intersection between the system axis and the axis of rotation during the scan,
selection of at least two points in the at least one CT image dataset which are on the connecting line, and
performance, in each case, of a removal of annular artifacts about each of the selected at least two points, wherein each of the at least two points are used as a center point of the annular artifacts to be removed.

12. The computer system as claimed in claim 11, wherein the computer program in the memory is designed in such a way that, in operation, it also performs:
calculating, from the at least one CT image dataset, at least one artifact image dataset by multiple filtering, containing only the image artifacts which arise from defective detector pixels;
subtracting the at least one artifact image dataset pixel-by-pixel from the at least one CT image dataset; and
at least one of displaying, storing and further processing a result of the subtraction.

13. A computer system designed for image processing, comprising:
a memory to store a computer program which, in operation, is adapted to perform at least the following:
receipt of at least one CT image dataset from detector data from spiral sampling with an inclined gantry, wherein image artifacts arising from defective detector pixels can be present in the at least one CT image dataset,
reconstruction of at least one CT image dataset from the detector data collected during a finite advance along the system axis, wherein image artifacts arising from defective detector pixels may be present in the at least one CT image dataset,
determination of a geometric position of a line, in the reconstructed at least one CT image dataset, which connects all points of intersection between the system axis and the axis of rotation during the scan,
selection of at least two points in the at least one CT image dataset which are on the connecting line, and
performance, in each case, of a removal of annular artifacts about each of the selected at least two points, wherein each of the at least two points are used as a center point of the annular artifacts to be removed.

14. The computer system as claimed in claim 13, wherein the computer program in the memory is designed in such a way that, in operation, it also performs:
calculating, from the at least one CT image dataset, at least one artifact image dataset by multiple filtering, containing only the image artifacts which arise from defective detector pixels;
subtracting the at least one artifact image dataset pixel-by-pixel from the at least one CT image dataset; and
at least one of displaying, storing and further processing a result of the subtraction.

* * * * *